US012650480B2

(12) United States Patent
Brickler et al.

(10) Patent No.: US 12,650,480 B2
(45) Date of Patent: Jun. 9, 2026

(54) RADIO FREQUENCY RECEIVING COIL ASSEMBLY WITH HANDLE

(71) Applicant: GE Precision Healthcare LLC, Wauwatosa, WI (US)

(72) Inventors: Monica Marie Brickler, Wauwatosa, WI (US); Daniel Rajan Chirayath, Bath Township, OH (US); Nabeel Manzar Malik, Solon, OH (US); Fraser John Laing Robb, Aurora, OH (US); Christopher Lee Siverly, Oconomowoc, WI (US); Zachery Kevin Steck, Streetsboro, OH (US); Janelle Teri Warrick, Wauwatosa, WI (US); Jana Michelle Vincent, Aurora, OH (US); Meghan Evelyn Blanks, Stow, OH (US)

(73) Assignee: GE Precision Healthcare LLC, Waukesha, WI (US)

( * ) Notice: Subject to any disclaimer, the term of this patent is extended or adjusted under 35 U.S.C. 154(b) by 977 days.

(21) Appl. No.: 17/858,466

(22) Filed: Jul. 6, 2022

(65) Prior Publication Data

US 2024/0012073 A1　　Jan. 11, 2024

(51) Int. Cl.
*G01R 33/34* (2006.01)
*A61B 5/055* (2006.01)
*G01R 33/3415* (2006.01)

(52) U.S. Cl.
CPC ........ *G01R 33/34084* (2013.01); *A61B 5/055* (2013.01); *G01R 33/3415* (2013.01)

(58) Field of Classification Search
CPC .......... G01R 33/34084; G01R 33/3415; G01R 33/3607; G01R 33/3621; G01R 33/3692; G01R 33/34007; G01R 33/34; G01R 33/36; G01R 33/48; A61B 5/055; A61B 5/0013
See application file for complete search history.

(56) References Cited

U.S. PATENT DOCUMENTS

| 3,376,618 | A | * | 4/1968 | Schwarzkopf | ..... B65D 33/1683 383/23 |
| 5,214,813 | A | * | 6/1993 | Gastle | ...................... A61G 1/01 5/625 |
| 5,409,282 | A | * | 4/1995 | Bale | ......................... A45C 3/00 294/146 |

(Continued)

OTHER PUBLICATIONS https://www.tecserena.com/en/upright-mri-coil/#abdominal-thoracic; downloaded Jul. 6, 2022; 4 pgs.

(Continued)

*Primary Examiner* — Pascal M Bui Pho
*Assistant Examiner* — Nicholas A Robinson
(74) *Attorney, Agent, or Firm* — Fletcher Yoder, P.C.

(57) ABSTRACT

A radio frequency (RF) receiving coil assembly for a magnetic resonance imaging (MRI) system includes a flexible enclosure. The RF receiving coil assembly also includes an RF coil disposed within the flexible enclosure, wherein the RF coil comprises a plurality of flexible loops having a malleable conductor. The RF receiving coil assembly further includes at least one cutout in the flexible enclosure located outside an area where the RF coil is disposed within the flexible enclosure. The at least one cutout is configured to provide a handle for handling the RF receiving coil assembly.

11 Claims, 12 Drawing Sheets

(56) References Cited

U.S. PATENT DOCUMENTS

| | | | |
|---|---|---|---|
| 7,873,145 B2 | 1/2011 | Liu et al. | |
| 2004/0141589 A1* | 7/2004 | Sharpensteen | G03B 42/025 |
| | | | 378/177 |
| 2011/0031970 A1* | 2/2011 | Ninomiya | A61B 5/704 |
| | | | 324/309 |
| 2012/0126814 A1* | 5/2012 | Fischer | G01R 33/30 |
| | | | 324/318 |
| 2016/0025798 A1* | 1/2016 | Takagi | G01R 35/00 |
| | | | 324/546 |
| 2017/0074955 A1* | 3/2017 | Choi | G01R 33/34007 |
| 2018/0289189 A1* | 10/2018 | Lazzi | A41D 1/002 |

OTHER PUBLICATIONS https://www.philips.co.uk/healthcare/product/HCNMRF158/dstreamtor; downloaded Jul. 6, 2022; 8 pgs.

* cited by examiner

RADIO FREQUENCY RECEIVING COIL ASSEMBLY WITH HANDLE

BACKGROUND

The subject matter disclosed herein relates to medical imaging and, more particularly, to a radio frequency (RF) coil assembly for a magnetic resonance imaging (MM) system, the RF coil assembly having a handle.

Non-invasive imaging technologies allow images of the internal structures or features of a patient/object to be obtained without performing an invasive procedure on the patient/object. In particular, such non-invasive imaging technologies rely on various physical principles (such as the differential transmission of X-rays through a target volume, the reflection of acoustic waves within the volume, the paramagnetic properties of different tissues and materials within the volume, the breakdown of targeted radionuclides within the body, and so forth) to acquire data and to construct images or otherwise represent the observed internal features of the patient/object.

During MM, when a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, or "longitudinal magnetization", $M_z$, may be rotated, or "tipped", into the x-y plane to produce a net transverse magnetic moment, $M_t$. A signal is emitted by the excited spins after the excitation signal $B_1$ is terminated and this signal may be received and processed to form an image.

When utilizing these signals to produce images, magnetic field gradients (Gx, $G_y$, and $G_z$) are employed. Typically, the region to be imaged is scanned by a sequence of measurement cycles in which these gradient fields vary according to the particular localization method being used. The resulting set of received nuclear magnetic resonance (NMR) signals are digitized and processed to reconstruct the image using one of many well-known reconstruction techniques.

Some RF coil assemblies utilized with MRI systems include multiple channels disposed within an enclosure. However, these RF coil assemblies lack an area for gripping them and carrying them around. This makes it awkward to carry the RF coil assemblies around when handling. In addition, these RF coil assemblies are laid out flat when stored which consumes a lot of space.

BRIEF DESCRIPTION

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In one embodiment, a radio frequency (RF) receiving coil assembly for an MRI system is provided. The RF receiving coil assembly includes a flexible enclosure. The RF receiving coil assembly also includes an RF coil disposed within the flexible enclosure, wherein the RF coil comprises a plurality of flexible loops having a malleable conductor. The RF receiving coil assembly further includes at least one cutout in the flexible enclosure located outside an area where the RF coil is disposed within the flexible enclosure. The at least one cutout is configured to provide a handle for handling the RF receiving coil assembly.

In another embodiment, an RF receiving coil assembly for an MRI system is provided. The RF receiving coil assembly includes a flexible enclosure. The RF receiving coil assembly also includes an RF coil disposed within the flexible enclosure, wherein the RF coil comprises a plurality of flexible loops having a malleable conductor. The RF receiving coil assembly further includes a first cutout and a second cutout in the flexible enclosure located outside an area where the RF coil is disposed within the flexible enclosure. The RF receiving coil assembly is configured to be folded over so that the first cutout and the second cutout align with each other to enable a single hand to hold the RF receiving coil assembly via the first cutout and the second cutout.

In a further embodiment, an RF receiving coil assembly for an Mill system is provided. The RF receiving coil assembly includes a flexible enclosure. The RF receiving coil assembly also includes an RF coil disposed within the flexible enclosure, wherein the RF coil comprises a plurality of flexible loops having a malleable conductor. The RF receiving coil assembly further includes a cutout located outside an area where the RF coil is disposed within the flexible enclosure. The RF receiving coil assembly still further includes a structure disposed within the cutout along a cutout perimeter, wherein the structure is configured to inductively charge the RF receiving coil assembly when the RF receiving coil is disposed adjacent a transmitting coil configured for inductive charging.

BRIEF DESCRIPTION OF THE DRAWINGS

These and other features, aspects, and advantages of the present subject matter will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

The present disclosure provides embodiments of an RF coil assembly (e.g., RF receiving coil assembly) that includes a means for handling the RF coil assembly. For example, the RF coil assembly includes an RF coil disposed within the flexible enclosure. The RF coil includes multiple flexible loops (e.g., channels or elements) having a malleable conductor. The flexible enclosure includes one or more cutouts in a region of the flexible enclosure outside an area where the RF coil is disposed. The one or more cutouts provide a handle for handling the RF coil assembly. In certain embodiments, the cutouts may be arranged so that when RF coil assembly is folded over (e.g., folded in half) the cutouts align to enable a single hand to hold the RF coil assembly via the cutouts. In certain embodiments, each cutout includes a structure disposed within it along a cutout perimeter to provide a handle. These cutouts and/or structures enable the RF coil assembly to be easily handled and carried around. In certain embodiments, these cutouts and/or structures enable the RF coil assembly to be hanged on a hanger. Indeed, one or more of the RF coil assemblies may be hanged (e.g., on a wall within an imaging room with the Mill scanner, on the magnet of the Mill scanner, in a closet, etc.) together to save space. In certain embodiments, the RF coil assembly may be configured to be utilized wirelessly with the Mill system during an Mill scan and the handles structures may enable the wireless RF coil assembly to be inductively charged (e.g., via a transmitter coil within the hangers or adjacent the hangers).

Figure 1:
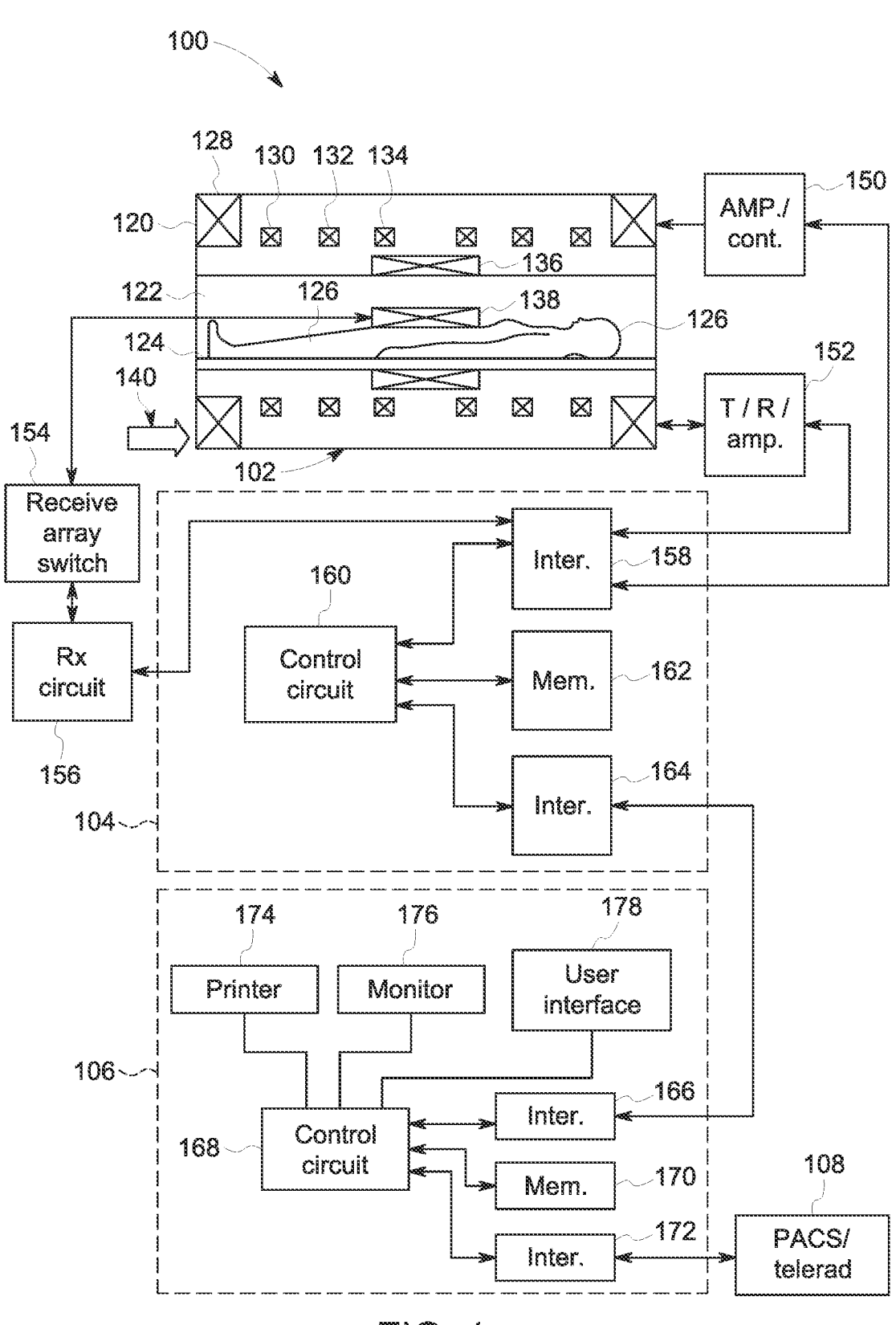
FIG. 1 illustrates an embodiment of a magnetic resonance imaging (MRI) system suitable for use with the disclosed technique.

With the preceding in mind, FIG. 1 a magnetic resonance imaging (MM) system 100 is illustrated schematically as including a scanner 102, scanner control circuitry 104, and system control circuitry 106. According to the embodiments described herein, the Mill system 100 is generally configured to perform MR imaging.

System 100 additionally includes remote access and storage systems or devices such as picture archiving and communication systems (PACS) 108, or other devices such as teleradiology equipment so that data acquired by the system 100 may be accessed on—or off-site. In this way, MR data may be acquired, followed by on- or off-site processing and evaluation. While the Mill system 100 may include any suitable scanner or detector, in the illustrated embodiment, the system 100 includes a full body scanner 102 having a housing 120 through which a bore 122 is formed. A table 124 is moveable into the bore 122 to permit a patient 126 to be positioned therein for imaging selected anatomy within the patient.

Scanner 102 includes a series of associated coils for producing controlled magnetic fields for exciting the gyromagnetic material within the anatomy of the subject being imaged. Specifically, a primary magnet coil 128 is provided for generating a primary magnetic field, $B_0$, which is generally aligned with the bore 122. A series of gradient coils 130, 132, and 134 permit controlled magnetic gradient fields to be generated for positional encoding of certain gyromagnetic nuclei within the patient 126 during examination sequences. A radio frequency (RF) coil 136 (e.g., RF transmit coil) is configured to generate radio frequency pulses for exciting the certain gyromagnetic nuclei within the patient. In addition to the coils that may be local to the scanner 102, the system 100 also includes a set of receiving coils or RF receiving coils 138 (e.g., an array of coils) configured for placement proximal (e.g., against) to the patient 126. As an example, the receiving coils 138 can include cervical/thoracic/lumbar (CTL) coils, head coils, single-sided spine coils, and so forth. Generally, the receiving coils 138 are placed close to or on top of the patient 126 so as to receive the weak RF signals (weak relative to the transmitted pulses generated by the scanner coils) that are generated by certain gyromagnetic nuclei within the patient 126 as they return to their relaxed state.

The various coils of system 100 are controlled by external circuitry to generate the desired field and pulses, and to read emissions from the gyromagnetic material in a controlled manner. In the illustrated embodiment, a main power supply 140 provides power to the primary field coil 128 to generate the primary magnetic field, $B_0$. A power input (e.g., power from a utility or grid), a power distribution unit (PDU), a power supply (PS), and a driver circuit 150 may together provide power to pulse the gradient field coils 130, 132, and 134. The driver circuit 150 may include amplification and control circuitry for supplying current to the coils as defined by digitized pulse sequences output by the scanner control circuitry 104.

Another control circuit 152 is provided for regulating operation of the RF coil 136. Circuit 152 includes a switching device for alternating between the active and inactive modes of operation, wherein the RF coil 136 transmits and does not transmit signals, respectively. Circuit 152 also includes amplification circuitry configured to generate the RF pulses. Similarly, the receiving coils 138 are connected to switch 154, which is capable of switching the receiving coils 138 between receiving and non-receiving modes. Thus, the receiving coils 138 resonate with the RF signals produced by relaxing gyromagnetic nuclei from within the patient 126 while in the receiving mode, and they do not resonate with RF energy from the transmitting coils (i.e., coil 136) so as to prevent undesirable operation while in the non-receiving mode. Additionally, a receiving circuit 156 is configured to receive the data detected by the receiving coils 138 and may include one or more multiplexing and/or amplification circuits.

It should be noted that while the scanner 102 and the control/amplification circuitry described above are illustrated as being coupled by a single line, many such lines may be present in an actual instantiation. For example, separate lines may be used for control, data communication, power transmission, and so on. Further, suitable hardware may be disposed along each type of line for the proper handling of the data and current/voltage. Indeed, various filters, digitizers, and processors may be disposed between the scanner and either or both of the scanner and system control circuitry 104, 106.

As illustrated, scanner control circuitry 104 includes an interface circuit 158, which outputs signals for driving the gradient field coils and the RF coil and for receiving the data representative of the magnetic resonance signals produced in examination sequences. The interface circuit 158 is coupled to a control and analysis circuit 160. The control and analysis circuit 160 executes the commands for driving the circuit 150 and circuit 152 based on defined protocols selected via system control circuit 106.

Control and analysis circuit 160 also serves to receive the magnetic resonance signals and performs subsequent processing before transmitting the data to system control circuit 106. Scanner control circuit 104 also includes one or more memory circuits 162, which store configuration parameters, pulse sequence descriptions, examination results, and so forth, during operation.

Interface circuit 164 is coupled to the control and analysis circuit 160 for exchanging data between scanner control circuitry 104 and system control circuitry 106. In certain embodiments, the control and analysis circuit 160, while illustrated as a single unit, may include one or more hardware devices. The system control circuit 106 includes an interface circuit 166, which receives data from the scanner control circuitry 104 and transmits data and commands back to the scanner control circuitry 104. The control and analysis circuit 168 may include a CPU in a multi-purpose or application specific computer or workstation. Control and analysis circuit 168 is coupled to a memory circuit 170 to store programming code for operation of the MM system 100 and to store the processed image data for later reconstruction, display and transmission. The programming code may execute one or more algorithms that, when executed by a processor, are configured to perform reconstruction of acquired data as described below. In certain embodiments, the memory circuit 170 may store one or more neural networks for reconstruction of acquired data as described below. In certain embodiments, image reconstruction may occur on a separate computing device having processing circuitry and memory circuitry.

An additional interface circuit 172 may be provided for exchanging image data, configuration parameters, and so forth with external system components such as remote access and storage devices 108. Finally, the system control and analysis circuit 168 may be communicatively coupled to various peripheral devices for facilitating operator interface and for producing hard copies of the reconstructed images. In the illustrated embodiment, these peripherals include a printer 174, a monitor 176, and user interface 178 including devices such as a keyboard, a mouse, a touchscreen (e.g., integrated with the monitor 176), and so forth.

Figure 2:
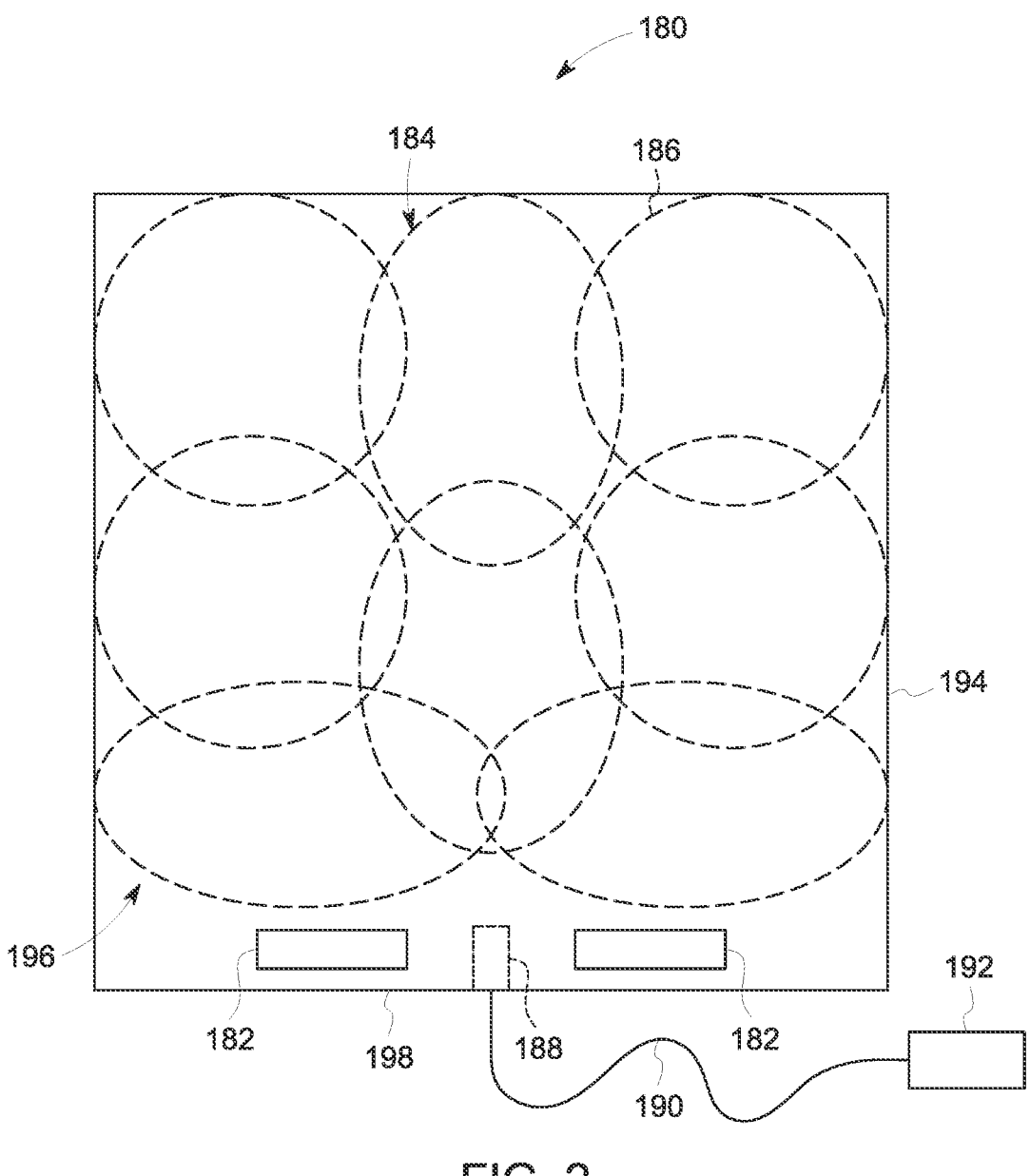
FIG. 2 is a schematic diagram of an RF coil assembly having cutouts for handles, in accordance with aspects of the present disclosure.

FIG. 2 is a schematic diagram of an RF coil assembly 180 (e.g., RF receiving coil assembly) having cutouts 182 for handles. The RF coil assembly 180 may be utilized in an MRI system (e.g., Mill system 100 in FIG. 1). The RF coil assembly 180 includes an RF coil 184 having a plurality of loops 186 (e.g., elements or channels). Each loop 186 is coupled to an electronics unit coupled to a coil-interfacing cable. The coil-interfacing cables of each of the loops 186 is coupled to an electrical connector interface or interface circuitry 188 (e.g., a balun such as integrated balun cable harness which may act as an RF trap). The electrical connector interface 188 is coupled (via a cable 190) to a P connector 192 (e.g., port connector) that enables the RF coil assembly 180 to be coupled (e.g., via wired connection) to the interface of the Mill system that couples imaging components to processing components. In certain embodiments, the RF coil assembly 180 may lack a wired connection and may be configured to be utilized wirelessly (e.g., for coupling imaging components to wireless components) with the MM system during an MRI scan.

Each loop 186 may consist of linked resonator elements coupled to a printed circuit board module (e.g., the electronics unit). Each electronics unit may include various components (e.g., a decoupling circuit, an impedance inverter circuit, and a pre-amplifier). The RF coil 184 may be designed utilizing AIR™ coil technology from General Electric Healthcare. This enables the RF coil 184 to be lightweight and flexible. Each loop 186 includes a malleable (e.g., flexible) conductor that enables complex and irregular surface contours. In certain embodiments, each loop 186 may stretch (e.g., due to a liquid metal conductor). Alternatively, each loop 186 may include litz wire, a regular stranded wire, or a spiral wire woven on an extendible non-conductive support or a meandering trace. In addition, the loops 186 of the RF coil 184 are transparent, thus, aiding signal-to-noise ratios.

The RF coil 184 is disposed within a flexible enclosure 194 (e.g., blanket). As depicted, the flexible enclosure 194 has a rectangular shape. In certain embodiments, the flexible enclosure 194 may have a square shape or other shape.

As depicted, the cutouts 182 are located in the flexible enclosure 194 outside an area 196 where the RF coil 184 is disposed within the flexible enclosure 194. The cutouts 182 each provide a handle for handling the RF coil assembly 180. The number of cutouts 182 in the flexible enclosure 194 may vary. For example, the number of cutouts 182 may be 1, 2, 3, 4, or more. As depicted, the cutouts 182 are located on a same side 198 of the flexible enclosure 194. In certain embodiments, the cutouts 182 are located on different sides of the flexible enclosure 194. In certain embodiments, the cutouts 182 are located on opposite sides of the flexible enclosure 194.

As depicted, the cutouts 182 flank the interface circuitry 188. As depicted, the interface circuitry 188 is disposed within the flexible enclosure 194. In certain embodiments, the interface circuitry 188 may be disposed outside the flexible enclosure 194.

Figure 3:
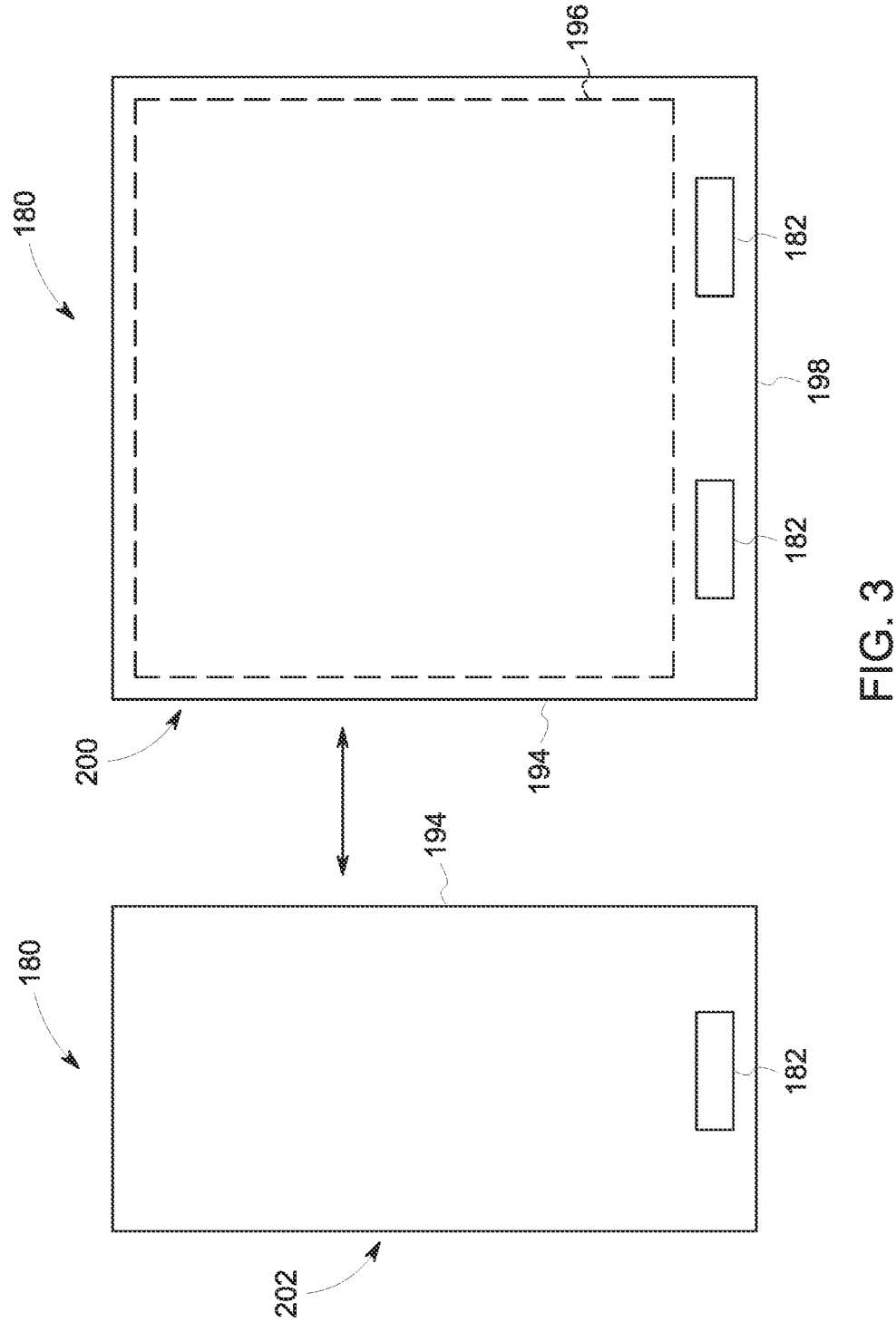
FIG. 3 is a schematic diagram of an RF coil assembly having cutouts disposed on a same side in a folded state and unfolded state, in accordance with aspects of the present disclosure.

In certain embodiments, the cutouts 182 are spaced apart on the same side 198 (outside the area 196 where the RF coil is located within the flexible enclosure 194) so that when the RF coil assembly 180 is folded over (e.g., folded in half) the cutouts 182 align with each other to enable a single hand to hold the RF coil assembly 180 via both the cutouts 182 as depicted in FIG. 3. The RF coil assembly 180 in FIG. 3 is configured for wireless operation with the MRI system. FIG. 3 depicts the RF coil assembly 180 in an unfolded state 200 and a folded state 202.

Figure 4:
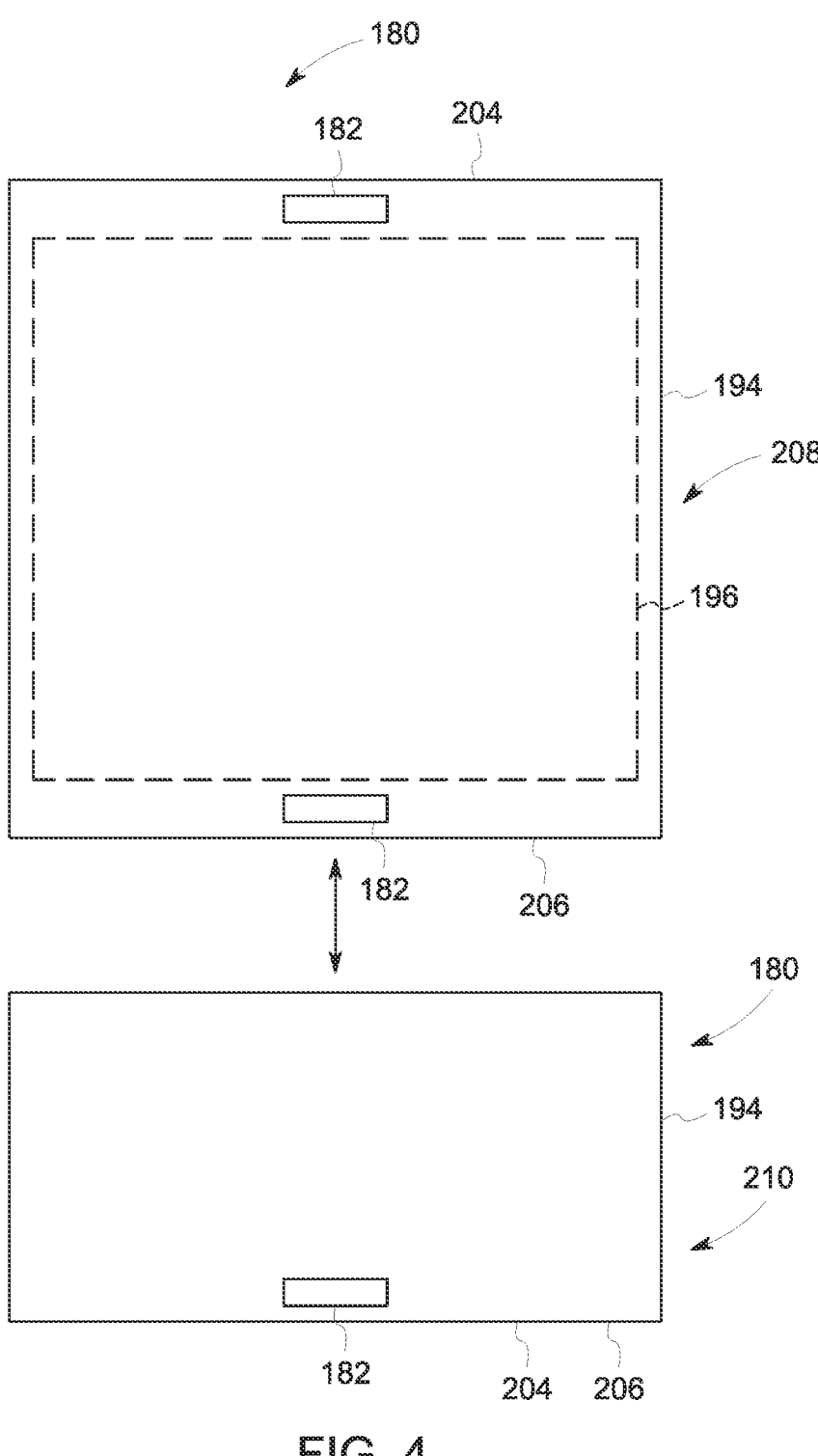
FIG. 4 is a schematic diagram of an RF coil assembly having cutouts disposed on opposite sides in a folded state and unfolded state, in accordance with aspects of the present disclosure.

FIG. 4 depicts an embodiment of the RF coil assembly 180 with the cutouts 182 located on opposite sides 204, 206 of the flexible enclosure 194 outside the area 196 where the RF coil is located within the flexible enclosure 194. The cutouts 182 are located on the opposite sides 204, 206 so that when the RF coil assembly 180 is folded over (e.g., folded in half) the cutouts 182 align with each other to enable a single hand to hold the RF coil assembly 180 via both the cutouts 182 as depicted in FIG. 4. The RF coil assembly 180 in FIG. 4 is configured for wireless operation with the MRI system. FIG. 4 depicts the RF coil assembly 180 in an unfolded state 208 and a folded state 210.

Figure 5:
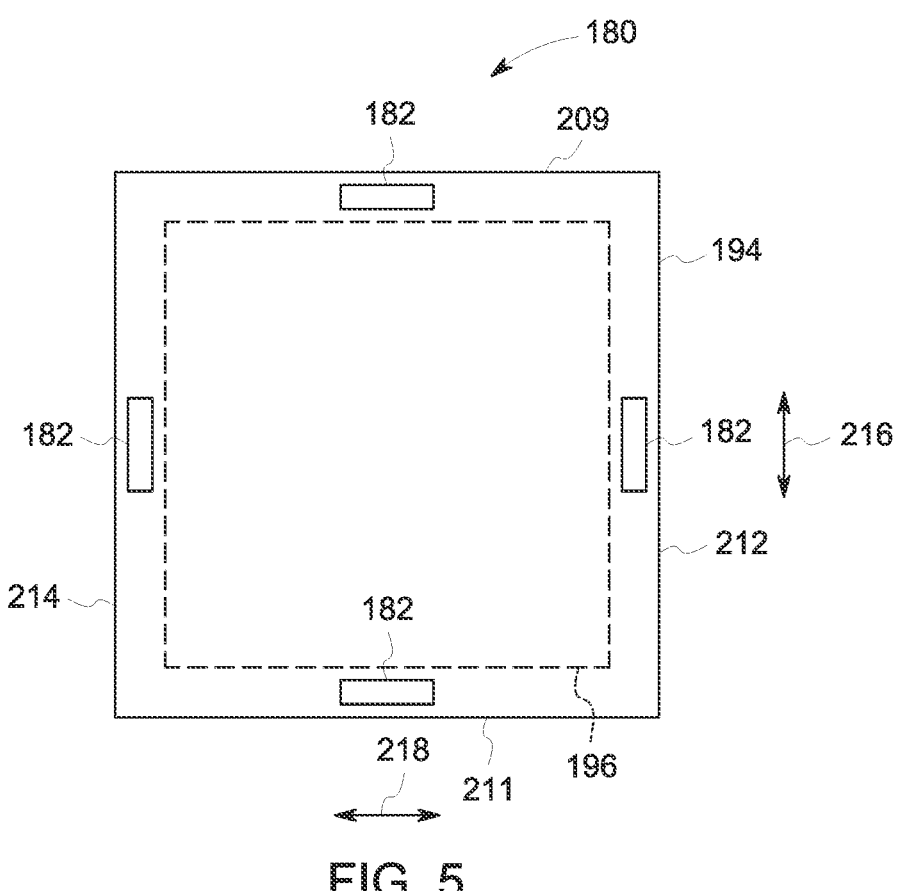
FIG. 5 is a schematic diagram of an RF coil assembly having cutouts disposed on all sides, in accordance with aspects of the present disclosure.

FIG. 5 depicts an embodiment of the RF coil assembly 180 with the cutouts 182 disposed on each side 209, 211, 212, 214 of the flexible enclosure 194 outside the area 196 where the RF coil is located within the flexible enclosure 194. The cutouts 182 on the sides 209, 211 may be aligned to enable a single hand to hold the RF coil assembly 180 when folding over the RF coil assembly 180 as indicated by arrow 216. The cutouts 182 on the sides 212, 214 may be aligned to enable a single hand to hold the RF coil assembly 180 when folding over the RF coil assembly 180 as indicated arrow 218. The RF coil assembly 180 in FIG. 5 is configured for wireless operation with the Mill system.

Figure 6:
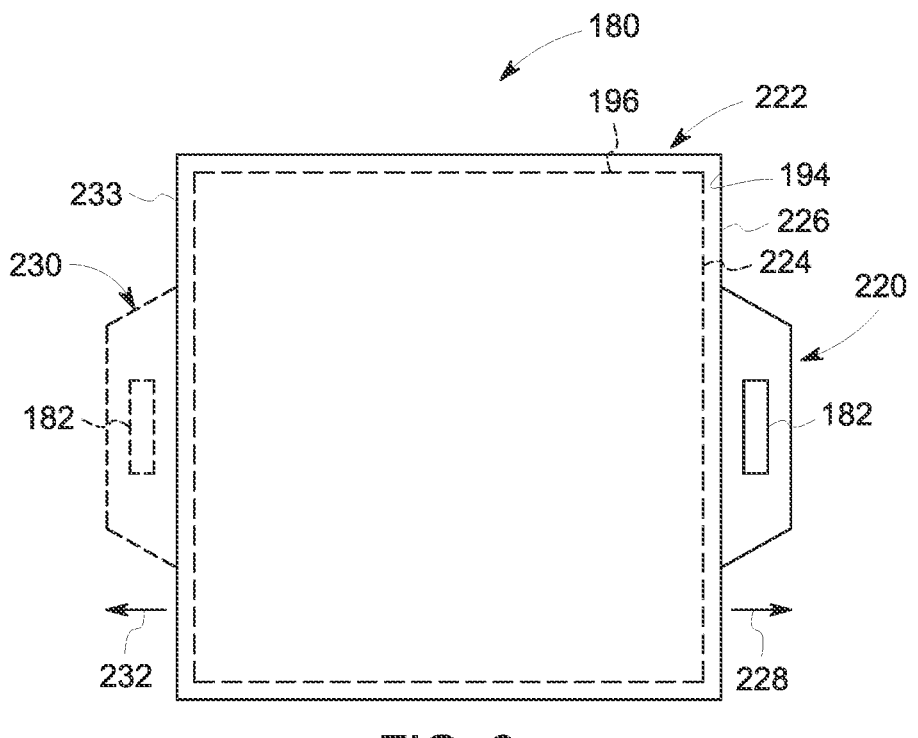
FIG. 6 is a schematic diagram of an RF coil assembly having an additional portion on the flexible enclosure having a cutout, in accordance with aspects of the present disclosure.

FIG. 6 is a schematic diagram of the RF coil assembly 180 having an additional portion 220 on the flexible enclosure 194 having the cutout 182. The flexible enclosure 194 includes a main portion 222 defined by a perimeter 224. The RF coil is disposed within the main portion 222 within the area 196. As depicted in FIG. 6, the area 196 extends across almost the entirety of the main portion 222. The additional portion 220 is located on a side 226 of the flexible enclosure 194. The additional portion 220 is outside the area 196. The additional portion 220 extends in a direction 228 away from the side 226 (and the main portion 222) beyond the perimeter 224. The additional portion 220 may be disposed along a portion or an entire length of the side 226. The cutout 182 is located within the additional portion 220. In certain embodiments, more than one cutout 182 may be located within the additional portion 220 to enable folding and handling of the RF coil assembly 180 as described in FIG. 3. In certain embodiments, other additional portions having cutouts 182 may be disposed on other sides of the flexible enclosure 194. For example, as depicted in FIG. 6, in certain embodiments, another additional portion 230 may be disposed on side 233 (e.g., opposite the side 226) of the main portion 222 of the flexible enclosure 194. The additional portion 230 is outside the area 196 and extends in a direction 232 away from the side 233 (and the main portion 222) beyond the perimeter 224. The cutouts 182 located on the additional portions 220, 230 enable folding and handling of the RF coil assembly 180 as described in FIG. 4.

Figure 7:
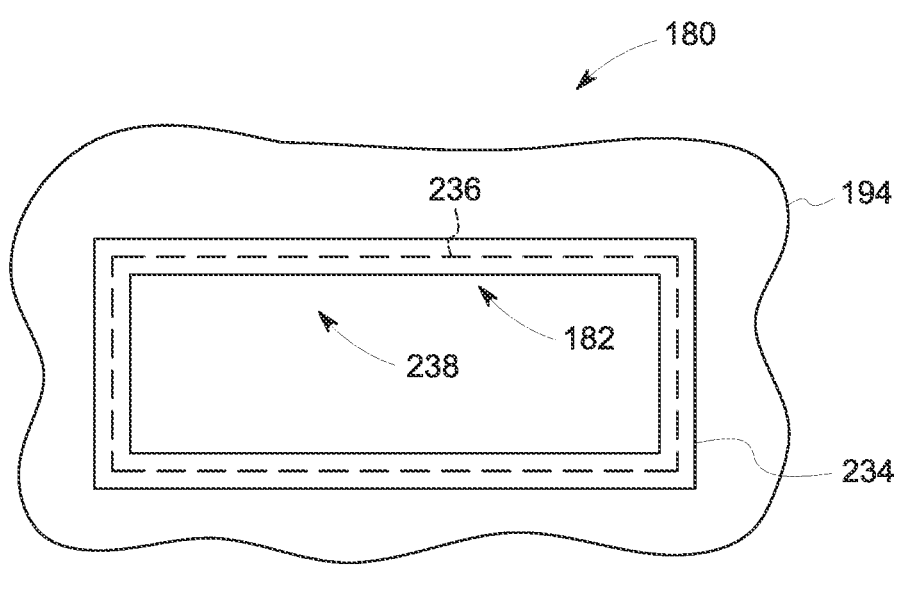
FIG. 7 is a schematic view of a portion of an RF coil assembly having a structure (e.g., handle structure) disposed within a cutout, in accordance with aspects of the present disclosure.

In certain embodiments, a structure (e.g., handle structure) may be disposed within the cutouts 182. FIG. 7 is a schematic view of a portion of the RF coil assembly 180 having a structure 234 disposed within the cutout 182. As depicted in FIG. 7, the structure 234 is disposed within the cutout 182 along a cutout perimeter 236. The structure 234 extends along the entire cutout perimeter 236. The structure 234 includes an opening 238 that enables the structure 234 to serve as a handle. The structure 234 may reinforce the region around the cutout 182. In certain embodiments, each cutout 182 of the RF coil assembly 180 may include a respective structure 234. In certain embodiments, only some of the cutouts 182 of the RF coil assembly 180 may include a respective structure 234. In certain embodiments, some or all of the cutouts 182 in the embodiments in FIGS. 2-6 above may include a respective structure 234.

Figure 8:
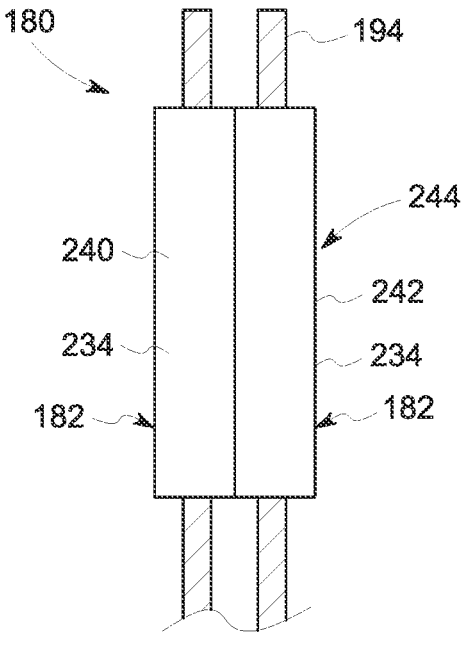
FIG. 8 is a schematic cross-sectional view of a portion of an RF coil assembly having structures (e.g., handle structures) coupled together to form a handle, in accordance with aspects of the present disclosure.

In embodiments, with cutout arrangements as shown in the RF coil assemblies in FIGS. 3 and 4, the cutouts 182 may each include a respective structure 234 (e.g., handle structure) (e.g., structures 240, 242) that may be coupled together as depicted in FIG. 8 to form a single handle 244. In certain embodiments, the respective structures 234 are coupled together via a snap fit. In certain embodiments, the respective structures 234 may be coupled together by a different mechanism.

Figure 9:
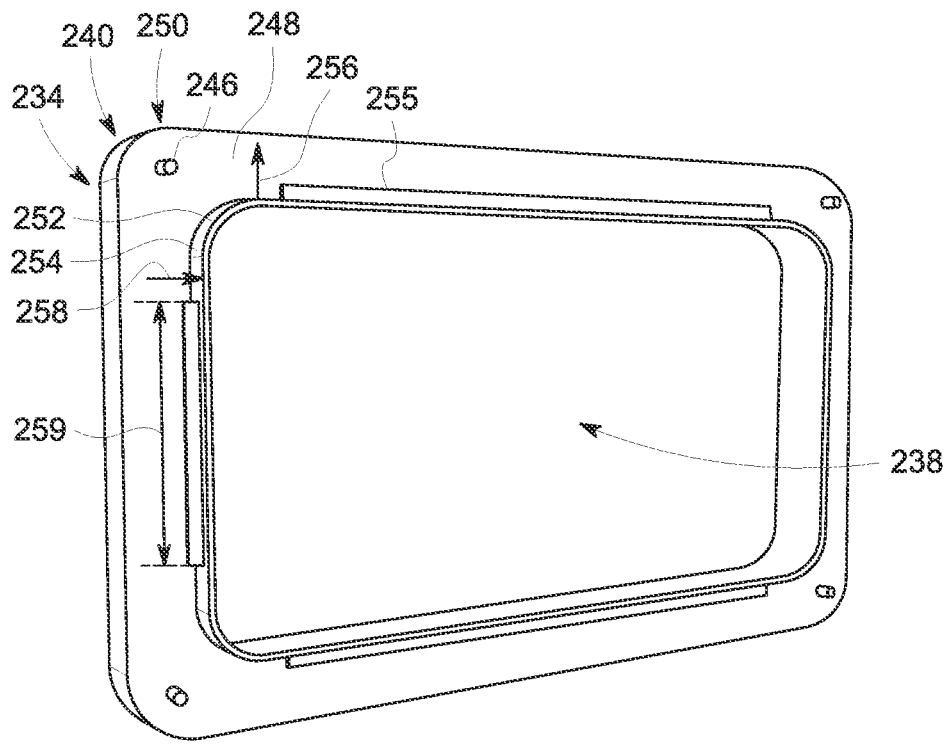
FIG. 9 is a perspective view of one of the structures in FIG. 8 (e.g., having prongs and tabs), in accordance with aspects of the present disclosure.
Figure 10:
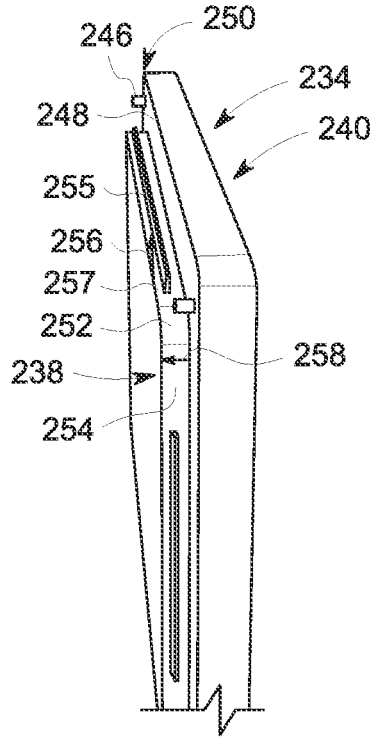
FIG. 10 is a perspective view of the structure in FIG. 9, in accordance with aspects of the present disclosure.

The structure 240 is depicted in FIGS. 9 and 10. As depicted in FIGS. 9 and 10, a plurality of prongs or protrusions 246 extend away from a surface 248 (e.g., configured to interface with the structure 242). The surface 248 extends completely around the opening 238. A single prong 246 is disposed adjacent each corner 250 of the structure 240 for a total of 4 prongs 246. In certain embodiments, the number and location of the prongs 246 on the surface 248 may vary. In addition, the structure 240 includes an extension portion 252 on the surface 248 that extends away from the surface 248. The extension portion 252 extends about the opening 238 adjacent a perimeter of the opening 238. Each side 254 of the extension portion 252 includes a tab or protrusion 255 that in a direction 256 that is orthogonal to a direction 258 that the extension portion 252 extends away from the surface 248. The tabs 255 are located on an outer surface 257 of the extension portion 252. As depicted, the tab 255 may taper in the direction 256. As depicted, the tab 255 extends along a portion of a length of the side 254. A length 259 of the tab 255 along a portion of the length of the side 254 may vary.

Figure 11:
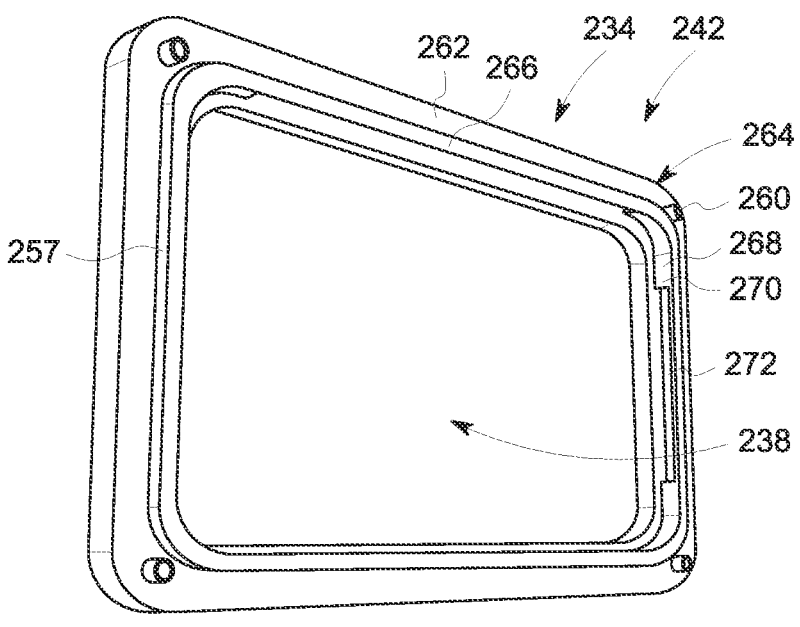
FIG. 11 is a perspective view of one of the structures in FIG. 8, (e.g., having receptacles), in accordance with aspects of the present disclosure.
Figure 12:
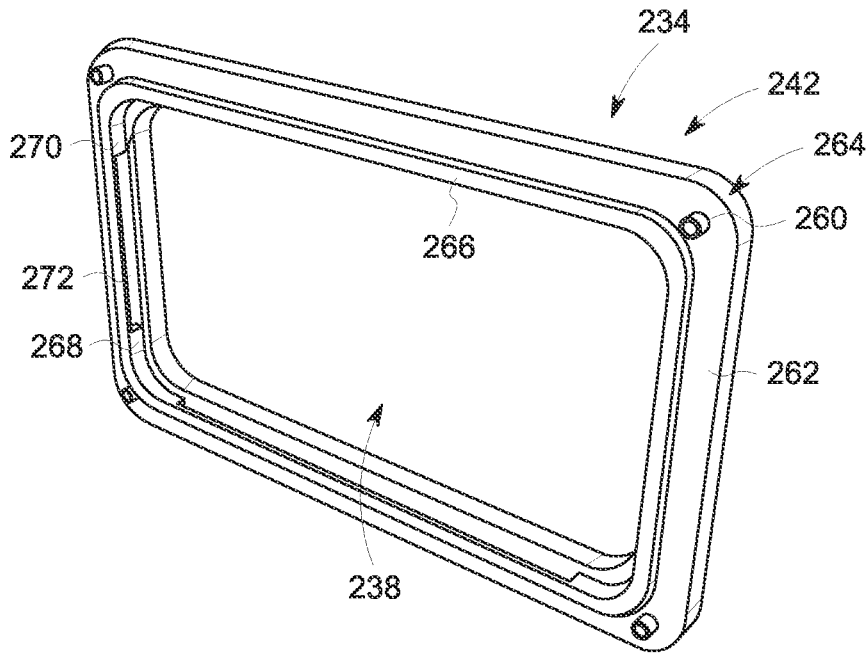
FIG. 12 is a perspective view of the structure in FIG. 11, in accordance with aspects of the present disclosure.

The structure 242 is depicted in FIGS. 11 and 12. As depicted, a plurality of receptacles 260 extend away from a surface 262 (e.g., configured to interface with the structure 240). The surface 262 extends completely around the opening 238. A single receptacle 260 is disposed adjacent each corner 264 of the structure 242 for a total of 4 receptacles 260. In certain embodiments, the number and location of the receptacles 260 may vary. The number and location of the receptacles 260 corresponds to the number and location of the prongs 246 of the structure 240 in FIGS. 9 and 10. The structure 242 includes an extension portion 266 on the surface 262 that extends away from the surface 262. The extension portion 266 includes an inner surface 268. Each side 270 of the inner surface 268 includes a slot or receptacle 272. During coupling of the structures 240, 242, the respective receptacles 260 are configured to receive the respective prongs 246 of the structure 240, while the respective slots 272 are configured to the receive the respective tabs 255 of the structure 240 to provide a snap fit. During coupling of the structures 240, 242, the outer surface 257 of the extension portion 252 of the structure 240 fits within the inner surface 268 of the extension portion 266 of the structure 242.

Figure 13:
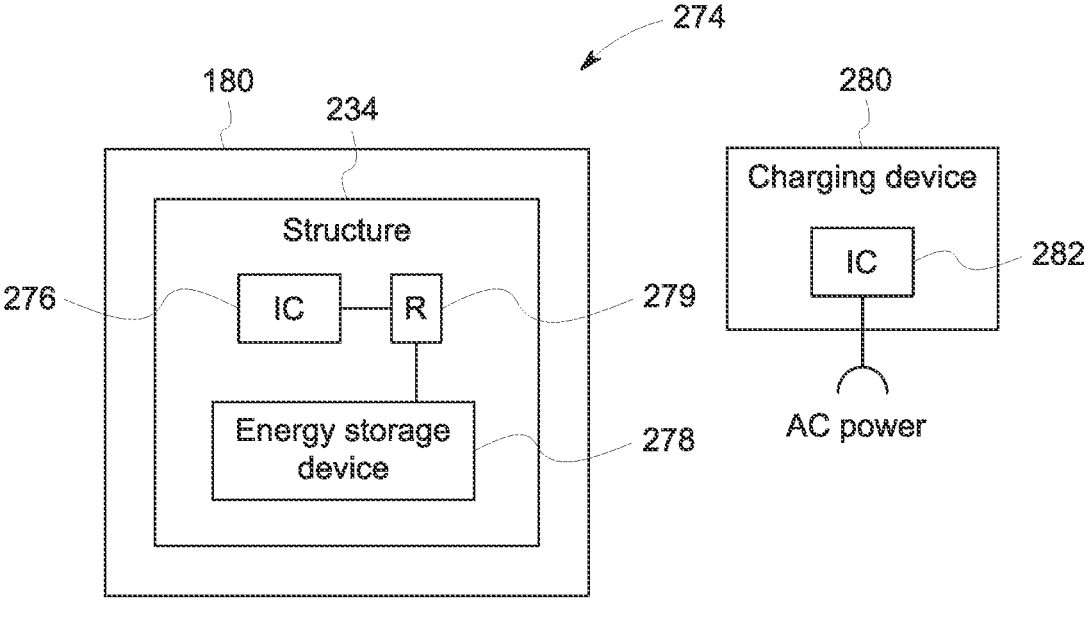
FIG. 13 is a schematic view of an inductive charging system for an RF coil assembly, in accordance with aspects of the present disclosure.

FIG. 13 is a schematic of an inductive charging system 274 for an RF coil assembly 180. In certain embodiments, the RF coil assembly 180 may be configured to be utilized wirelessly with the Mill system during an MRI scan. In certain embodiments, one or more of the handles structures 234 disposed within respective cutouts may enable the wireless RF coil assembly 180 to be inductively charged. The structure 234 may include an inductive coil 276 (e.g., inductive charge receive or receiving coil). The structure 234 includes an energy storage device 278 (e.g., supercapacitor such as a lithium-ion capacitor) for storing power coupled to the inductive coil 276. The energy storage device 278 is configured to be inductively charged. The energy storage device 278 powers the electrical components of the RF coil assembly 180. The structure 234 may include other electrical circuits for inductive charging (e.g., rectifier for converting alternating current (AC) to direct current (DC) that is provided to the energy storage device 278). The inductive coil 276 is configured to generate a current (e.g., AC current) in response to a transmitted magnetic field. In certain embodiments, the RF coil assembly 180 may lack the structure 234 and the components (e.g., the inductive coil 276, the energy storage device 278, and the rectifier 279) for inductive charging may be disposed within the flexible enclosure of the RF coil assembly 180 adjacent the cutout.

The inductive charging system 274 includes a charging device 280 for inductively charging the RF coil assembly 180. In certain embodiments, the charging device 280 may be in one or more hangers that the RF coil assembly 180 is hung on via the structures 234. In certain embodiments, the charging device 280 may be a charging pad disposed adjacent the hangers (e.g., between the hangers). The charging device 280 includes an inductive coil 282 (e.g., transmitting coil) that may transmit a magnetic field. The charging device 280 receives an alternating current that generates the magnetic field that induces the alternating current in the inductive coil 276.

Figure 14:
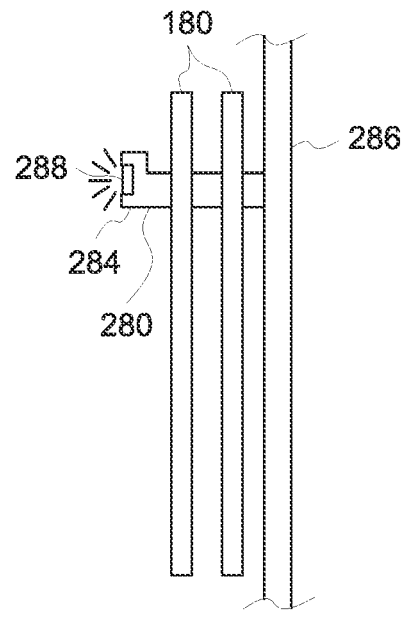
FIG. 14 is a schematic side view of RF coil assemblies being inductively charged, in accordance with aspects of the present disclosure.
Figure 15:
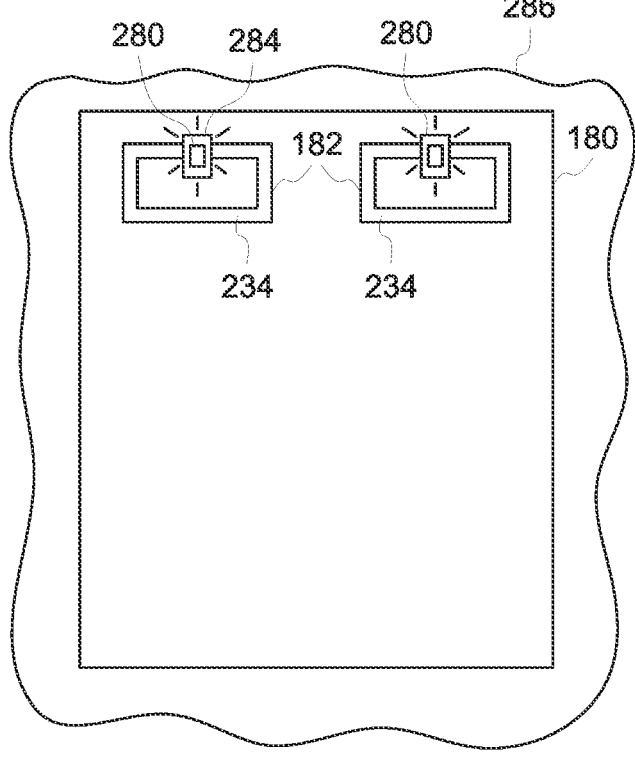
FIG. 15 is a schematic front view of an RF coil assemblies being inductively charged, in accordance with aspects of the present disclosure.

FIGS. 14 and 15 are schematic views of the RF coil assemblies 180 being inductively charged. The RF coil assemblies 180 each include structures 234 disposed within cutouts 182. The structures 234 are as described in FIG. 13 for inductive charging. The RF coil assemblies 180 are hung on hangers 284 coupled to a wall 286 (e.g., in the room for conducting the imaging scan). In certain embodiments, the RF coil assemblies 180 may include a single structure 234 and be hung on a single hanger 284. The hangers 284 increase storage space within a room by enabling the hanging of the one or more RF coil assemblies 180. Hanging the RF coil assemblies 180 takes up less space than storing the RF coil assemblies 180 in a flat position. Hanging the RF coil assemblies 180 also provides easy access to the RF coil assemblies 180.

The hangers 284 serve as the charging device 280 as described in FIG. 13. In particular, components of the charging device 280 (e.g., the inductive coil 282) are disposed within the hangers 284. The hangers 284 may be provided AC power. In certain embodiments, where a single RF coil assembly 180 is hung on multiple hangers 284, only a single hanger 284 may be utilized to charge the RF coil assembly 180. In certain embodiments, where a single RF coil assembly 180 is hung on multiple hangers 284 each of the hangers 284 (or multiple hangers 284) may be utilized to charge the RF coil assembly 180. Utilizing multiple hangers 284 for charging enables faster charging of the RF coil assembly 180. Similarly, when multiple RF coil assemblies 180 are hung on multiple hangers 284, a single hanger 284 or each of the hangers 284 may be utilized to charge the multiple RF coil assemblies 180.

Each hanger 284 that may be utilized for charging RF coil assemblies 180 may include a light emitting device 288 for emitting light when the hanger 284 is in the process of charging the RF coil assembly 180. The light emitting device 288 may be coupled to the charging device 280 within the hanger 284. Upon hanging the RF coil assemblies 180 on the hangers 284, light may be emitted from the light emitting device 288. In certain embodiments, when one or more of the RF coil assemblies 180 is at less than a fully charged state, the light emitting device 288 may intermittently emit light (e.g., flash). In certain embodiments, when each RF coil assembly 180 hanging on the one or more hangers 284 is fully charged, the light emitting device 288 may continuously emit light. In certain embodiments, when one or more of the RF coil assemblies 180 is at less than a fully charged state, the light emitting device 288 may continuously emit light or intermittently emit light in a first color (e.g., red). Upon each of the RF coil assemblies 180 hanging on the one or more hangers 284 being fully charged, the light emitting device 288 may continuously emit light or intermittently emit light a second color (e.g., blue) different from the first color.

In certain embodiments, where the one or more RF coil assemblies 180 are hanging on multiple hangers 284, each hanger 284 may emit light from its respective light emitting device 288 when charging the RF coil assemblies 180. In certain embodiments, where the one or more RF coil assemblies 180 are hanging on multiple hangers 284, only the one or more hangers 284 being utilized to charge the one or more RF coil assemblies 180 may emit light from their respective light emitting devices 288.

Figure 16:
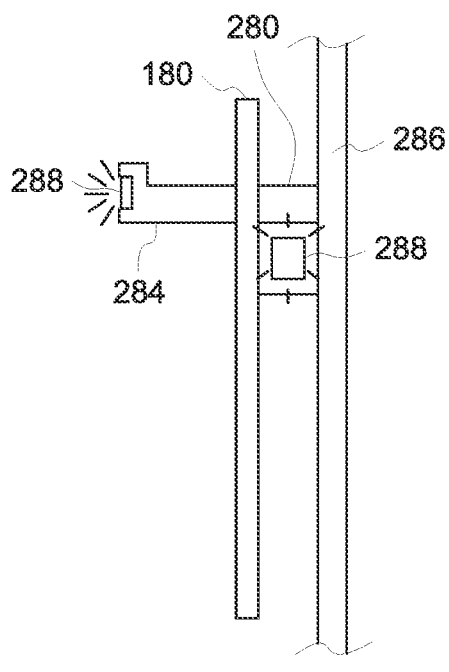
FIG. 16 is a schematic side view of the RF coil assembly being inductively charged (e.g., via charging device on wall), in accordance with aspects of the present disclosure.
Figure 17:
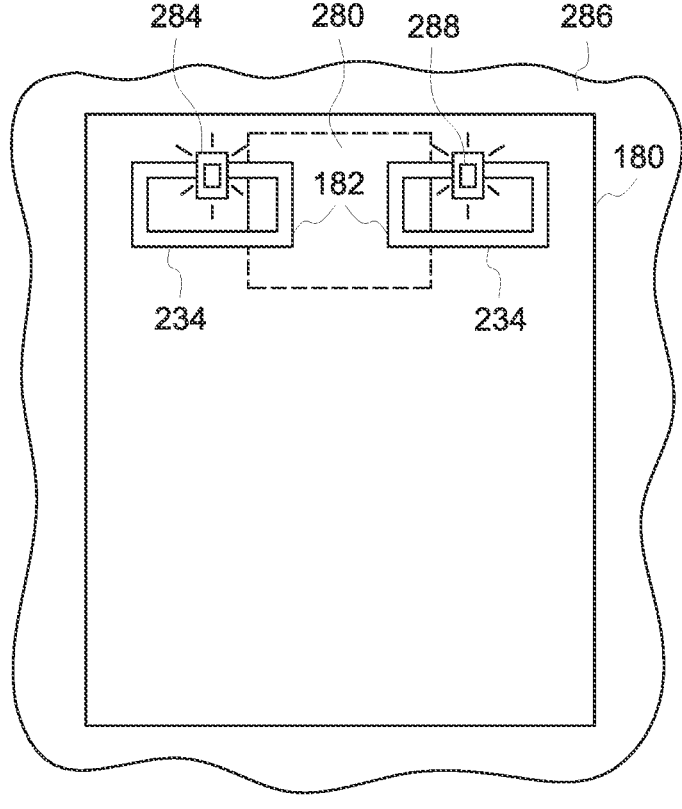
FIG. 17 is a schematic front view of the RF coil assembly being inductively charged (e.g., via charging device on wall), in accordance with aspects of the present disclosure.

FIGS. 16 and 17 are schematic views of the RF coil assembly 180 being inductively charged (via the charging device 280 located on the wall 286). The RF coil assembly 180 includes structures 234 disposed within cutouts 182. The structures 234 are as described in FIG. 13 for inductive charging. The RF coil assembly 180 is hung on hangers 284 coupled to the wall 286 (e.g., in the room for conducting the imaging scan). In certain embodiments, the RF coil assembly 180 may include a single structure 234 and be hung on a single hanger 284. The hangers 284 increase storage space within a room by enabling the hanging of the one or more RF coil assemblies 180. Hanging the RF coil assembly 180 takes up less space than storing the RF coil assembly 180 in a flat position. Hanging the RF coil assembly 180 also provides easy access to the RF coil assembly 180.

Instead of the hangers 284 acting as a charging device (e.g., as shown in FIGS. 16 and 17), a separate charging device 280 is disposed on the wall adjacent the hangers 284. The charging device 280 is as described in FIG. 13. The charging device 280 may be provided AC power. The RF coil assembly 180 is charged by hanging the RF coil assembly on the hangers 284 adjacent the charging device 280.

In certain embodiments, may include the light emitting device 288 coupled to the charging device 280. In certain embodiments, the light emitting device 288 may be located on the charging device 280. The light emitting device 288 emits light when the RF coil assembly 180 is being charged. Upon hanging the RF coil assembly 180 on the hangers 284 adjacent the charging device 280, light may be emitted from the light emitting device 288. In certain embodiments, when the RF coil assembly 180 is at less than a fully charged state, the light emitting device 288 may intermittently emit light (e.g., flash). In certain embodiments, when the RF coil assembly 180 hanging on the one or more hangers 284 is fully charged, the light emitting device 288 may continuously emit light. In certain embodiments, when the RF coil assembly 180 is at less than a fully charged state, the light emitting device 288 may continuously emit light or intermittently emit light in a first color (e.g., red). Upon the RF coil assembly 180 being fully charged, the light emitting device 288 may continuously emit light or intermittently emit light a second color (e.g., blue) different from the first color.

Figure 18:
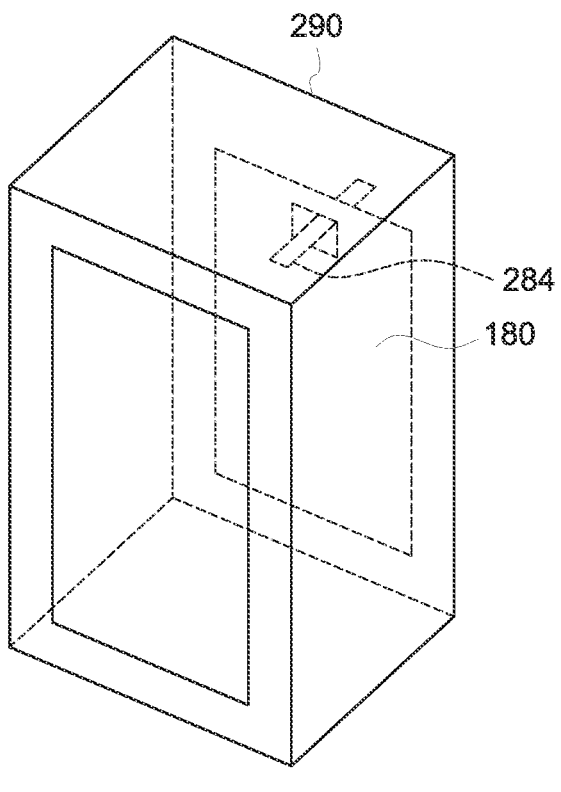
FIG. 18 is a perspective view of an RF coil assembly being disposed within a cabinet or closet, in accordance with aspects of the present disclosure.

Besides being hung on a wall (e.g., in the imaging room), the RF coil assemblies 180 may be disposed in in other locations. FIG. 18 is a perspective view of the RF coil assembly 180 being disposed within a cabinet or closet 290. As depicted in FIG. 18, one or more RF coil assemblies 180 may be disposed within the cabinet or closet 290. In particular, one or more RF coil assemblies 180 may be hung on one or more hangers 284 within the cabinet or closet 290. The cabinet or closet 290 may be located within the imaging room. Hanging the RF coil assemblies 180 within the cabinet or closet 290 saves storage space. In certain embodiments, the cabinet or closet 290 may include a charging device for inductively charging the RF coil assemblies 180 within the cabinet or closet 290 as described above. For example, the charging device may be incorporated within the one or more hangers 284 or disposed on a wall of the cabinet or closet 290.

Figure 19:
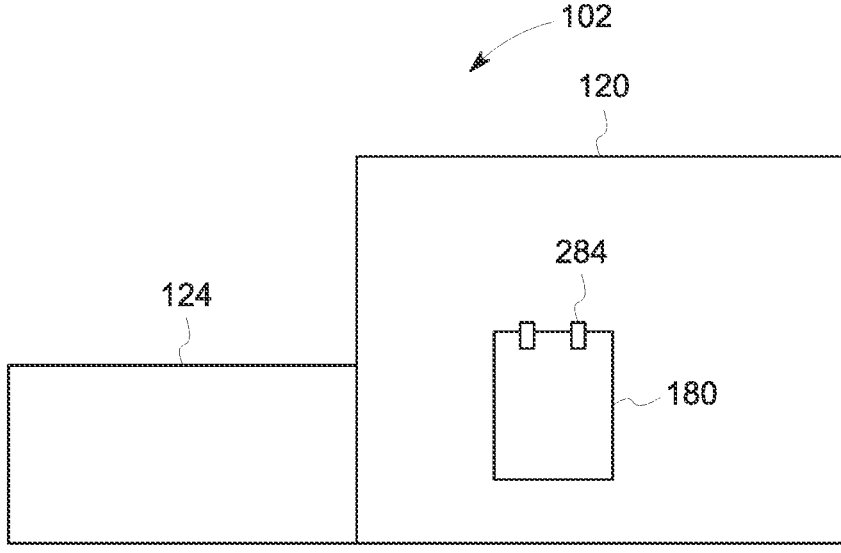
FIG. 19 is a schematic view of an RF coil assembly being disposed on a side of a housing of an MRI scanner, in accordance with aspects of the present disclosure.

FIG. 19 is a schematic view of the RF coil assembly 180 being disposed on a side of the housing 120 of the Mill scanner 102 (e.g., the magnet of the MM scanner). The housing 120 may include one or more hangers 284 disposed on its side. One or more RF coil assemblies 180 may be hung on the one or more hangers 284. Hanging the RF coil assemblies 180 on the housing 120 saves storage space. In certain embodiments, the housing 120 may include a charging device for inductively charging the RF coil assemblies 180 as described above. For example, the charging device may be incorporated within the one or more hangers 284 or disposed on side of the housing 120.

Technical effects of the disclosed subject matter include providing an RF coil assembly including one or more cutouts and/or handle structures disposed within the cutouts outside an area where the RF coil is disposed. The one or more cutouts and/or handle structures enable the RF coil assembly to be easily handled and carried around in an ergonomic manner. In addition, these cutouts and/or handle structures enable one hand to be free (as normally two hands are typically used to carry an RF coil assembly without cutouts or handle structures) for multitasking (e.g., patient help, setup, cleanup, etc.). These cutouts and/or handle structures enable one or more of the RF coil assemblies to be hanged on one or more hangers (e.g., on a wall within an imaging room with the MM scanner, on the magnet of the MRI scanner, in a closet, etc.) together to save space while providing easy access to the RF coil assemblies. In certain embodiments, the RF coil assembly may be configured to be utilized wirelessly with the MRI system during an MM scan and the handle structures may enable the wireless RF coil assembly to be inductively charged (e.g., via a transmitter coil within the hangers or adjacent the hangers). Further, these cutouts and/or handle structures enables easy testing of the durability of the RF coil assemblies since it is known how most users will carry the RF coil assemblies (e.g., via the cutouts and/or handle structures).

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

This written description uses examples to disclose the present subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A radio frequency (RF) receiving coil assembly for a magnetic resonance imaging (MRI) system, comprising:
   a flexible enclosure;
   an RF coil disposed within the flexible enclosure, wherein the RF coil comprises a plurality of flexible loops having a malleable conductor; and
   a first cutout disposed entirely within a flexible portion of the flexible enclosure, wherein the first cutout is located outside an area where the RF coil is disposed within the flexible enclosure; and
   a first handle structure disposed within the first cutout along a first cutout perimeter, and the first handle structure is configured to provide a first handle for handling the RF receiving coil assembly via a first opening in the first handle structure, wherein the first opening is located within the first cutout within the flexible portion of the flexible enclosure, and wherein the RF receiving coil assembly is configured to be inductively charged via the first handle structure when the RF receiving coil assembly is disposed adjacent to a transmitting coil configured for inductive charging.

2. The RF receiving coil assembly of claim 1, wherein the flexible enclosure comprises a main portion defined by a perimeter that houses the RF coil, the flexible enclosure comprises an aditional portion that extends in a direction away from the main portion beyond the perimeter, and the first cutout is located on the additional portion.

3. The RF receiving coil assembly of claim 1, wherein the RF receiving coil assembly is configured to be utilized wirelessly with the MRI system during an MRI scan.

4. The RF receiving coil assembly of claim 1, wherein the RF receiving coil assembly comprises a second cutout disposed entirely within the flexible portion of the flexible enclosure located outside the area where the RF coil is disposed within the flexible enclosure.

5. The RF receiving coil assembly of claim 4, wherein the RF receiving coil assembly is configured to be folded over so that the first cutout and the second cutout align with each other to enable a single hand to hold the RF receiving coil assembly via the first cutout and the second cutout.

6. The RF receiving coil assembly of claim 5, wherein the RF receiving coil assembly comprises the first handle structure disposed within the first cutout along the first cutout perimeter and a second handle structure disposed within the second cutout along a second cutout perimeter, and the first handle structure is configured to be coupled to the second handle structure to form a single handle for handling the RF receiving coil assembly via respective openings in the first handle structure and the second handle structure.

7. The RF receiving coil assembly of claim 6, wherein the first handle structure is configured to be coupled to the second handle structure via a snap fit.

8. The RF receiving coil assembly of claim 5, wherein the RF receiving coil assembly is configured to be utilized via a wired connection with the MRI system during an MRI scan.

9. The RF receiving coil assembly of claim 8, wherein the RF receiving coil assembly comprises interface circuitry disposed within the flexible enclosure and coupled to both the RF coil and the wired connection, and the first cutout and the second cutout flank the interface circuitry.

10. A radio frequency (RF) receiving coil assembly for a magnetic resonance imaging (MRI) system, comprising:

a flexible enclosure;

an RF coil disposed within the flexible enclosure, wherein the RF coil comprises a plurality of flexible loops having a malleable conductor; and a first cutout and a second cutout each disposed entirely within a flexible portion of the flexible enclosure, wherein the first cutout and the second cutout are located outside an area where the RF coil is disposed within the flexible enclosure, wherein the RF receiving coil assembly comprises a first handle structure disposed within the first cutout along a first cutout perimeter and a second handle structure disposed within the second cutout along a second cutout perimeter, and wherein the RF receiving coil assembly is configured to be folded over so that a first opening in the first handle structure and a second opening in the second handle structure align with each other to enable a single hand to hold the RF receiving coil assembly via both the first opening in the first handle structure and the second opening in the second handle structure, wherein the first opening is located within the first cutout within the flexible portion of the flexible enclosure and the second opening is located within the second cutout within the flexible portion of the flexible enclosure, and wherein at least one of the first handle structure and the second handle structure is configured to inductively charge the RF receiving coil assembly when the RF receiving coil assembly is disposed adjacent to a transmitting coil configured for inductive charging.

11. The RF receiving coil assembly of claim 10, wherein the RF receiving coil assembly is configured to be utilized wirelessly with the MRI system during an MRI scan.

* * * * *